United States Patent
Bougamont et al.

(10) Patent No.: US 6,318,549 B1
(45) Date of Patent: Nov. 20, 2001

(54) DEVICE FOR PACKAGING AND TREATING BACTERICIDE FOR CONTACT LENSES

(75) Inventors: Jean-Louis Bougamont; Pascal Hennemann, both of Eu; David Leuliet, Mers les Bains, all of (FR)

(73) Assignee: Rexam Sofab, Le Treport (FR)

( * ) Notice: Subject to any disclaimer, the term of this patent is extended or adjusted under 35 U.S.C. 154(b) by 0 days.

(21) Appl. No.: 09/647,912
(22) PCT Filed: Apr. 13, 1999
(86) PCT No.: PCT/FR99/00858
 § 371 Date: Oct. 13, 2000
 § 102(e) Date: Oct. 13, 2000
(87) PCT Pub. No.: WO99/52568
 PCT Pub. Date: Oct. 21, 1999

(30) Foreign Application Priority Data

Apr. 14, 1998 (FR) .................................................. 98 04612

(51) Int. Cl.[7] .................................................. A45C 11/04
(52) U.S. Cl. .............................. 206/5.1; 134/901; 422/300
(58) Field of Search ........................ 206/5.1, 205, 210; 15/104.92, 104.93, 214, 244.1; 134/901; 422/28, 30, 292, 300; 435/264; 510/112–115

(56) References Cited

U.S. PATENT DOCUMENTS

| 4,942,959 | 7/1990 | Sauber et al. | 206/5.1 |
| 5,199,559 | 4/1993 | Dark | 206/5.1 |
| 5,439,572 | 8/1995 | Pankow | 206/5.1 |
| 5,657,506 | 8/1997 | Pankow | 206/5.1 |

FOREIGN PATENT DOCUMENTS

| 0049767-A2 | 4/1982 | (EP) . |
| 0830865-A2 | 3/1998 | (EP) . |
| WO-95/26756-A2 | 10/1995 | (WO) . |
| WO-96/36371-A1 | 11/1996 | (WO) . |

*Primary Examiner*—Luan K. Bui
(74) *Attorney, Agent, or Firm*—Bacon & Thomas, PLLC

(57) ABSTRACT

The invention relates to a packaging and bactericidal treatment device for contact lenses (L), said device being characterized in that it comprises: firstly a housing (1) provided with at least one cavity (10) receiving a support element (11) which has bactericidal action and whose outside face (11a) has curvature matching the curvature of the contact lenses (L); and secondly, at least one lid (2) designed to cover said cavity (10) and whose inside face is provided with at least one socket (20) which is suitable for being engaged in guided manner into said cavity (10), and which receives a wedge element (21) having bactericidal action and whose outside face (21a) has curvature complementary to the curvature of the support element (11) so that it protects and/or decontaminates a contact lens (L) by holding it stationary in said cavity (10) between said support element (11) and said wedge element (21).

14 Claims, 2 Drawing Sheets

DEVICE FOR PACKAGING AND TREATING BACTERICIDE FOR CONTACT LENSES

Figure 1A:
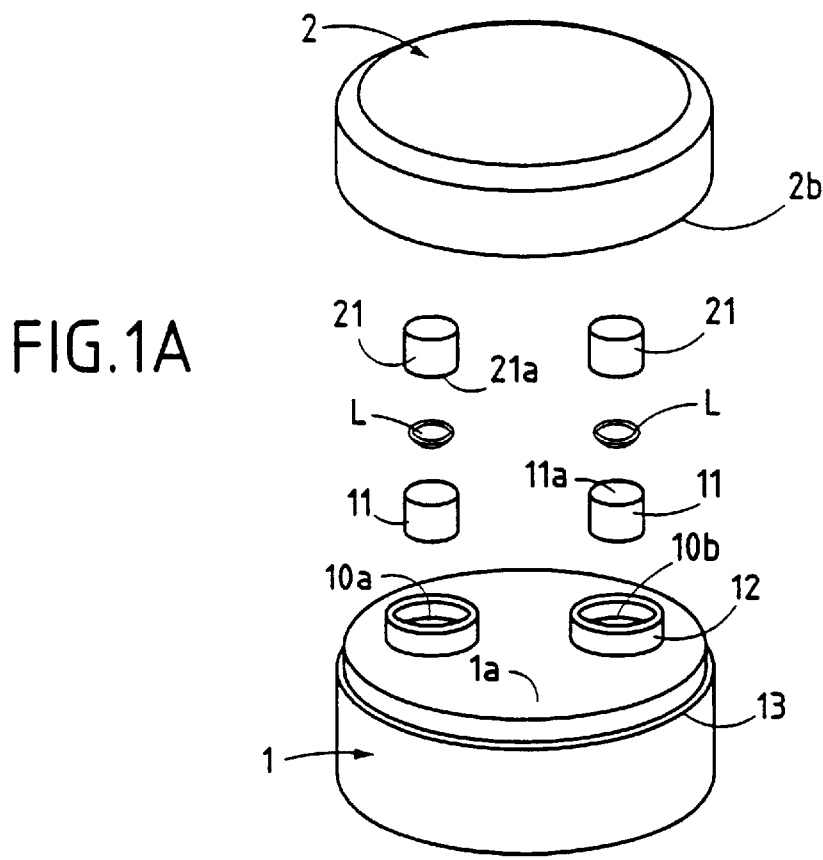

The present invention relates to a packaging and bactericidal treatment device for contact lenses.

In order to avoid any infection of the eyes, it is essential for contact lenses to be protected from any bacterial contamination, or else to be decontaminated before they are put in place on the cornea.

That is why devices exist for enabling contact lenses to be immersed in a bactericidal treatment solution. Such a device includes, in particular, means for suspending said contact lenses, which means are generally associated with means for closing the container of bactericidal solution.

Unfortunately, those devices are impractical.

The container of treatment liquid is difficult to transport, in particular since said container is generally small.

In addition, in the event of a handling error, the contact lenses fall to the bottom of the container, and are difficult to retrieve.

Furthermore, if the closure means are not locked properly, the container is not sealed properly, and bactericidal fluid can leak out, which can adversely affect the protection both of the contact lenses and also of the user.

Moreover, after immersion, the contact lenses, which are curved to some extent, sometimes retain very small amounts of bactericidal solution.

Unfortunately, bactericidal solutions generally contain a preservative agent which causes undesirable side effects on the human organism.

An object of the present invention is to solve the preceding technical problems satisfactorily by providing bacterial decontamination and protection by means of the packaging itself.

The invention achieves this object by means of a packaging and bactericidal treatment device for contact lenses, said device being characterized in that it comprises:

firstly a housing provided with at least one cavity receiving a support element which has bactericidal action and whose outside face has curvature matching the curvature of the contact lenses; and secondly, at least one lid designed to cover said cavity and whose inside face is provided with at least one socket which is suitable for being engaged in guided manner into said cavity, and which receives a wedge element having bactericidal action and whose outside face has curvature complementary to the curvature of the support element so that it protects and/or decontaminates a contact lens by holding it stationary in said cavity between said support element and said wedge element.

According to an advantageous characteristic, said support element and said wedge element are made of a porous material containing a non-migrant anti-bacterial agent.

According to another characteristic, said wedge element is radially clamped in the socket.

According to yet another characteristic, the edge of said cavity is provided with a collar whose inside wall is provided with a bevel serving to guide the socket.

Similarly, the peripheral edge of the socket is provided with a guide bevel.

Preferably, the end wall of the cavity is provided with a bore of small diameter and in which the support element is radially clamped.

Provision is made for the outside face of the support element to be concave, and for the outside face of the wedge element to be convex and to project beyond the peripheral edge of the socket.

In a specific embodiment, the support element and the wedge element are removable cylinders having the same diameter.

The respective dimensions of the cavity and of the socket are determined so that the outside wall of said socket comes into sliding contact with the inside wall of said cavity.

In a particular embodiment, the housing is provided with two cavities.

In a first variant embodiment, the device has a single lid which is provided with two sockets designed to be inserted into said cavities, and which is assembled to the housing by interfitting with peripheral radial clamping, so that the resulting assembly forms an accurately circularly symmetrical cylinder.

In a second variant, the device has two lids (2a, 2b), each of which is provided with a respective socket (20a, 20b).

In order to reinforce the biological protection, the housing and the lid(s) may be made of a plastics material containing a non-migrant anti-bacterial agent.

The device of the invention is of simple structure and it is easy to use, while it also improves, in particular, contact lens deposition and extraction. It offers full safety for storing and transporting lenses even in the event that it is subjected to impact, to being tipped over, or to the housing being turned upside down.

The device thus gives contact lenses mechanical and bacterial protection that is highly effective.

In addition, the device forms packaging that is particularly ergonomic and aesthetically pleasing.

Figure 1B:
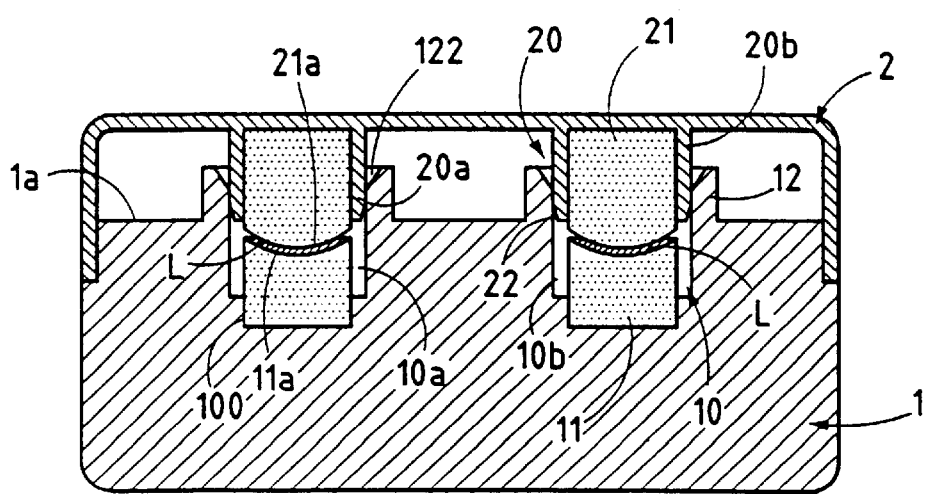
Figure 2A:
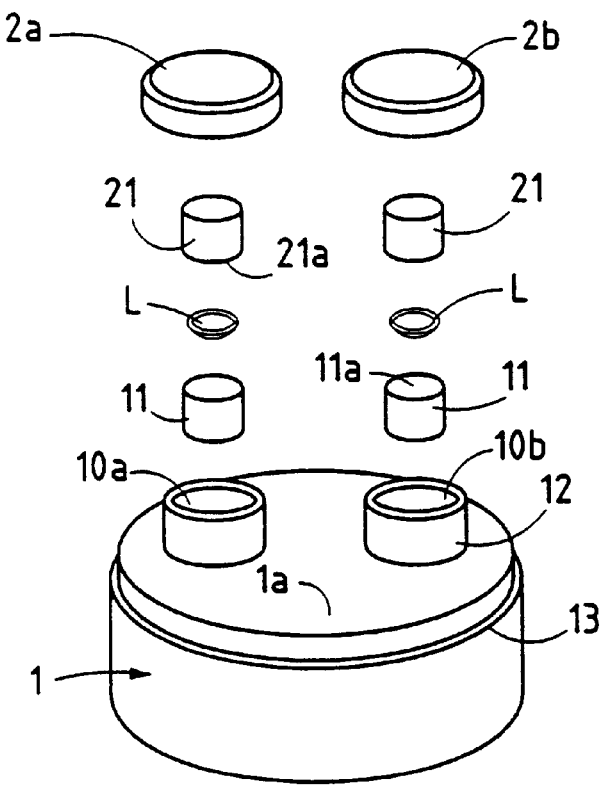
Figure 2B:
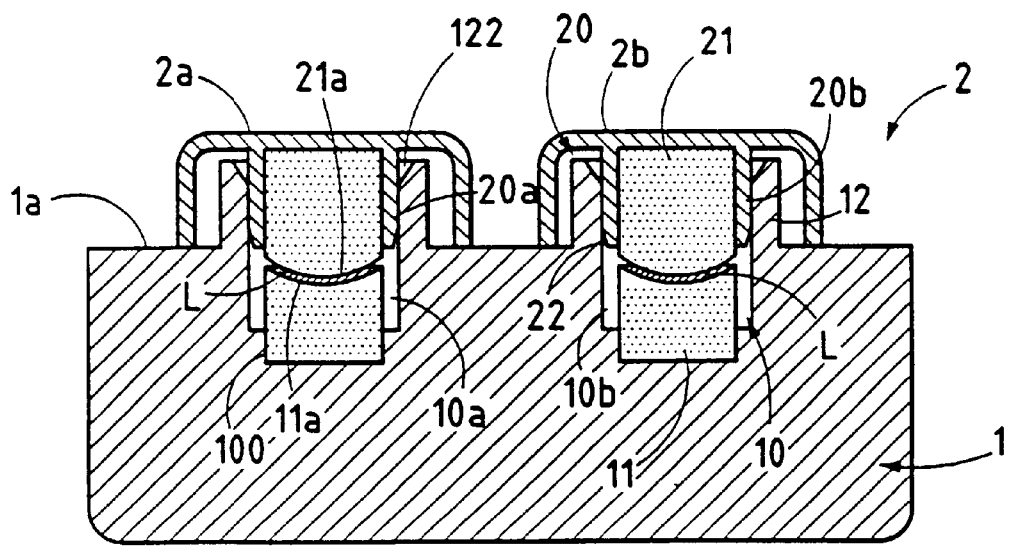

The invention will be better understood on reading the following description accompanied by the drawings, in which:

FIGS. 1a and 1b are views of a first embodiment of the device of the invention, respectively in exploded perspective and in cross-section; and FIGS. 2a and 2b are views of a second embodiment of the device of the invention, respectively in exploded perspective, and in cross-section.

The device shown in the figures serves to provide packaging and bactericidal treatment for contact lenses L.

The device includes a housing 1 provided with at least one cavity 10. In the present example, it has two cavities 10a and 10b.

A respective support element 11 for supporting a contact lens L is received in each cavity 10. The top face 11a of each support element has curvature matching the curvature of said contact lenses.

When the housing 1 is standing on a horizontal plane, the contact lenses L lie on the preferably concave top faces of the support elements 11, as shown in FIG. 2.

The device includes at least one lid 2 serving to cover the cavities 10a and 10b.

In the embodiment shown in FIGS. 1a and 1b, the lid is a single lid that covers both cavities simultaneously.

In the embodiment shown in FIGS. 2a and 2b, each cavity 10a, 10b is covered by an independent lid 2a, 2b.

In FIGS. 1a and 1b, the inside face of the lid 2 is provided with at least one socket 20. In this example, it is provided with two sockets 20a, 20b suitable for being engaged in guided manner into respective ones of the cavities 10a, 10b in the housing 1.

Each of the sockets 20a, 20b receives a respective wedge element 21 whose bottom outside face 21a has curvature that is complementary to the curvature of the support element 11 and that is therefore convex in this example.

In general, the number, the positions, and the dimensions of the sockets 20 match those of the cavities 10.

The support elements 11 and the wedge elements 21 are made of a plastics material that is preferably porous and that has a bactericidal action.

This material may be a plastics material containing a non-migrant anti-bacterial agent, e.g. based on silver, which performs the bactericidal treatment, and more precisely the bacterial decontamination, merely by being in contact with the facing face of the contact lens L.

Preferably, the housing 1, the lid 2, or the lids 2a, 2b are also made, e.g. by molding, of a plastics material containing a non-migrant anti-bacterial agent.

This configuration makes it possible to protect and/or to decontaminate the contact lenses L by holding each of them stationary inside a respective cavity 10 between a support element 11 and a wedge element 21, regardless of the three-dimensional angular position of the device.

The support elements 11 and the wedge elements 21 are cylinders of the same diameter. The end wall of the cavity 10 is provided with a bore 100 of small diameter and in which the support element 11 is fixed by radial clamping accompanied by slight resilient compression.

The edge of the cavity 10 is provided with a collar 12 which projects from the top face 1a of the housing 1.

The inside wall of the collar 12 and in particular its top edge is provided with a frustoconical bevel 12a serving to facilitate inserting the socket 20 into the cavity 10 by guiding it.

The height of the support element 11 is determined as a function of the height of the collar 12 and of the respective depths of the cavity 10 and of the bore 100, so that its concave outside face 11a is situated below the level of the top face 1a of the housing 1.

The wedge element 21 is also fixed in the socket 20, optionally in removable manner, by radial clamping accompanied by resilient compression.

The outside face 21a of the wedge element 21 projects beyond the peripheral edge of the socket 20 so that the edge of the socket does not touch the contact lens L.

Preferably, the outside face of the support element 11 is concave so as to stabilize the contact lens L, while the outside face of the wedge element 21 is convex so that it presses lightly against the contact lens, thereby preventing any displacement.

The peripheral edge of the socket 20 is provided with a frustoconical bevel co-operating with the bevel 122 of the collar 12 of the housing 1, and having a profile complementary to the profile of the bevel 122, so as to guide the socket 20 into the collar 12 by sliding contact.

The respective dimensions of the cavity 10 and of the socket 20 are determined so that, on putting the lid 2 in place on the housing 1, the outside side wall of the socket 20 comes into sliding contact with the inside wall of the cavity 10.

In the embodiment shown in FIGS. 1a and 1b, the housing 1 and the lid 2 are made independently and they are assembled together by interfitting with peripheral radial clamping, thereby forming an accurately circularly symmetrical cylinder.

For this purpose, the housing 1 is provided with a shoulder 13d serving to receive the bottom edge of the side wall of the lid 2 in flush manner.

In the embodiment of FIGS. 2a and 2b, each lid 2a and 2b is provided with a respective socket 20a, 20b and the bottom edges of the side walls of the lids come into abutment against the top face 1a of the housing.

In a variant (not shown), the lid 2 is joined to the housing 1, e.g. by means of a hinge. This variant may also be applied the embodiment having two lids as shown in FIGS. 2a and 2b, by fixing the hinge(s) to the top face of the housing.

For example, the contact lenses L can be extracted from the housing by turning the housing 1 upside down so that it then lies at the top of the device, and by separating it from the cover 2 which then lies below it on a horizontal plane.

Since the concave face 21a of the wedge element 21 projects from the socket 20, the contact lens L is then easily accessible to the user.

What is claimed is:

1. A packaging and bactericidal treatment device for contact lenses (L), said device being characterized in that it comprises:

firstly a housing (1) provided with at least one cavity (10) receiving a support element (11) which has bactericidal action and whose outside face (11a) has curvature matching the curvature of the contact lenses (L); and secondly, at least one lid (2) designed to cover said cavity (10) and whose inside face is provided with at least one socket (20) which is suitable for being engaged in guided manner into said cavity (10), and which receives a wedge element (21) having bactericidal action and whose outside face (21a) has curvature complementary to the curvature of the support element (11) so that it protects and/or decontaminates a contact lens (L) by holding it stationary in said cavity (10) between said support element (11) and said wedge element (21).

2. A device according to claim 1, characterized in that said support element (11) and said wedge element (21) are made of a porous material containing a non-migrant anti-bacterial agent.

3. A device according to claim 1, characterized in that said wedge element (21) is radially clamped in the socket (20).

4. A device according to claim 1, characterized in that the edge of said cavity (10) is provided with a collar (12) whose inside wall is provided with a bevel (122) serving to guide the socket (20).

5. A device according to claim 1, characterized in that the end wall of the cavity (10) is provided with a bore (100) of small diameter and in which the support element (11) is radially clamped.

6. A device according to claim 1, characterized in that the peripheral edge of the socket (20) is provided with a guide bevel (22).

7. A device according to claim 1, characterized in that the outside face (11a) of the support element (11) is concave.

8. A device according to claim 1, characterized in that the outside face (21a) of the wedge element (21) projects beyond the peripheral edge of the socket (20).

9. A device according to claim 1, characterized in that the support element (11) and the wedge element (21) are removable cylinders having the same diameter.

10. A device according to claim 1, characterized in that the respective dimensions of the cavity (10) and of the socket (20) are determined so that the outside wall of said socket comes into sliding contact with the inside wall of said cavity.

11. A device according to claim 1, characterized in that the housing (1) is provided with two cavities (10a, 10b).

12. A device according to claim 11, characterized in that it has a single lid (2) which is provided with two sockets (20a, 20b) designed to be inserted into said cavities, and which is assembled to the housing (1) by interfitting with peripheral radial clamping, so that the resulting assembly forms an accurately circularly symmetrical cylinder.

13. A device according to claim 11, characterized in that it has two lids (2a, 2b), each of which is provided with a respective socket (20a, 20b).

14. A device according to claim 1, characterized in that the housing (1) and the lid (2) are made of a plastics material containing a non-migrant anti-bacterial agent.

* * * * *